United States Patent
Lin et al.

(10) Patent No.: US 8,263,799 B2
(45) Date of Patent: Sep. 11, 2012

(54) CHIRAL BINAPHTHYL COMPOUNDS

(75) Inventors: Jian-Wen Lin, Taoyuan County (TW);
Chun-Ming Wu, New Taipei (TW);
Shih-Hsien Liu, Hsinchu County (TW);
Kung-Lung Cheng, Hsinchu (TW)

(73) Assignee: Industrial Technology Research Institute, Hsinchu (TW)

(*) Notice: Subject to any disclaimer, the term of this patent is extended or adjusted under 35 U.S.C. 154(b) by 0 days.

(21) Appl. No.: 13/094,834

(22) Filed: Apr. 27, 2011

(65) Prior Publication Data

US 2012/0165528 A1 Jun. 28, 2012

(30) Foreign Application Priority Data

Dec. 23, 2010 (TW) ................ 99145587 A

(51) Int. Cl.
*C07C 69/767* (2006.01)
*C07D 403/12* (2006.01)
(52) U.S. Cl. .................. 560/81; 544/296
(58) Field of Classification Search .......... 560/60, 560/81; 544/296
See application file for complete search history.

(56) References Cited

U.S. PATENT DOCUMENTS

| 5,139,698 A | 8/1992 | Plach et al. |
| 6,511,719 B2 | 1/2003 | Farrand |
| 7,318,950 B2 | 1/2008 | Kirsch et al. |
| 2008/0272337 A1 | 11/2008 | Farrand |

OTHER PUBLICATIONS

Merz, Conformer and Rotamers of trans-2,3-bis(2-naphthyl)-15-crown-5- and 18-crown-6 and their alkali metal complexes, 1998, European Journal of Organic Chemistry, p. 403-408.*
Stodulski, Synthesis of Yb Complexes with Amino-Acid-Armed Ligands for Direct Asymmetric Tandem Aldol Reduction Reactions, 2008, European Journal of Organic Chemistry, 553-5562.*
Yokota, Chirality Induction in Cyclocopolymerization, 1999, Polymer Journal, vol. 31, No. 11-2, p. 1037-1040.*

* cited by examiner

*Primary Examiner* — Golam M M Shameem
*Assistant Examiner* — Karen Cheng
(74) *Attorney, Agent, or Firm* — Jianq Chyun IP Office

(57) ABSTRACT

The present invention relates to chiral binaphthyl compounds having good solubility and high helical twisting power. The chiral binaphthyl compounds as dopants in the liquid crystal compositions can help enhance the display quality of the liquid crystal panels.

4 Claims, No Drawings

CHIRAL BINAPHTHYL COMPOUNDS

CROSS-REFERENCE TO RELATED APPLICATION

This application claims the priority benefit of Taiwan application serial no. 99145587, filed Dec. 23, 2010. The entirety of the above-mentioned patent application is hereby incorporated by reference herein and made a part of this specification.

BACKGROUND OF THE INVENTION

1. Field of the Invention

The present invention generally relates to chiral compounds. More particularly, the present invention relates to chiral binaphthyl compounds used in the liquid crystal compositions.

2. Description of Related Art

For the commonly used liquid crystal display (LCD) devices, various types of LCD devices can be classified based on the operation mode of liquid crystals or the driving mode, including twisted nematic (TN) display devices, super twisted nematic (STN) display devices, surface-stabilized cholesteric texture (SSCT) display devices, polymer-stabilized cholesteric texture (PSCT) display devices and thin film transistor (TFT) display devices.

The displaying quality of the liquid crystal display devices is essential and can be evaluated by several parameters, such as voltage holding ratio (VHR) and residual direct current voltage (Vrdc). If VHR is low, the voltage applied to the liquid crystal during the frame time will be lowered, leading to decreased brightness or even hindering the normal displaying of gray level. On the other hand, if Vrdc is too large, a residual image may be generated, that is, an image retention effect after voltage application.

SUMMARY OF THE INVENTION

The present invention is directed to chiral binaphthyl compounds having good solubility and high helical twisting power (HTP). The chiral binaphthyl compounds can be applied in the liquid crystal compositions. By mixing with the liquid crystals in various ratios, the liquid crystal composition containing chiral binaphthyl compounds of the present invention can afford high voltage holding ratios, thus lessening the image retention and improving the display contrast of the liquid crystal devices.

The present invention provides chiral binaphthyl compounds having the structure of the following formula (I):

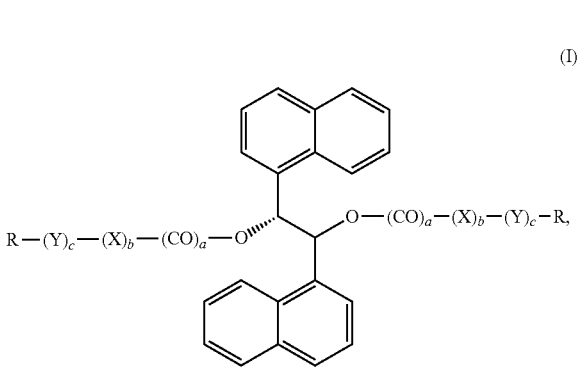

(I)

wherein Y is a repeating unit represented as $—(A^1—Z)m—A^2—$, $A^1$ and $A^2$ can be cyclic structures respectively selected from the following group:

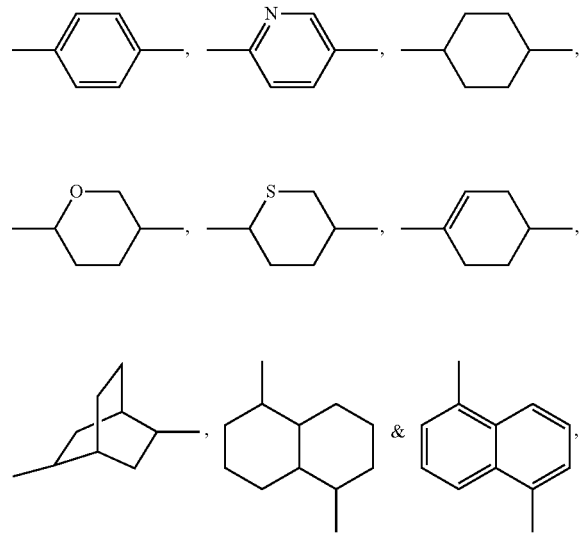

X and Z can be the same or different linking groups selected from the following group consisting of
—O—, —S—, —CO—, —COO—, —OCO—, —O—COO—, —CO—N($R^1$)—, —N($R^1$)—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=CH—, —CF=CH—, —CH=CF—, —CF=CF—, —C≡C—, —CH=CH—COO— and a single bond, a, b & c are individually 0, 1 or 2, m is 0, 1, 2 or 3, and R is a straight-chained or branched $C_1~C_{30}$ alkyl group, a straight-chained or branched $C_1~C_{30}$ alkyl group of which one or more —CH$_2$— being substituted with —O—, —S—, —NH—, —N(CH$_3$)—, —CO—, —CO—O—, —O—CO—, —CH=CH— or —C≡C—, or the above-mentioned alkyl group being selectively substituted with —F, —Cl, —Br, —NCS, —CN, or —OCF$_3$.

According to an embodiment of the present invention, the chiral binaphthyl compound is of the following chemical structure, wherein R=$C_5H_{11}$

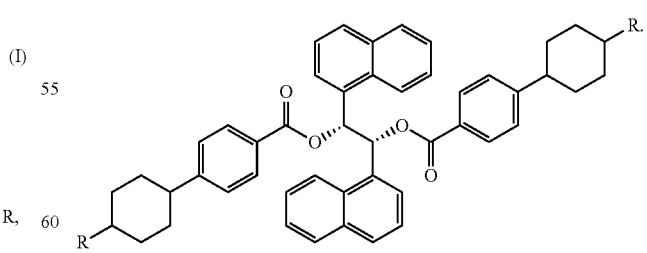

According to another embodiment of the present invention, the chiral binaphthyl compound can have the following chemical structure, wherein R=$C_7H_{15}$

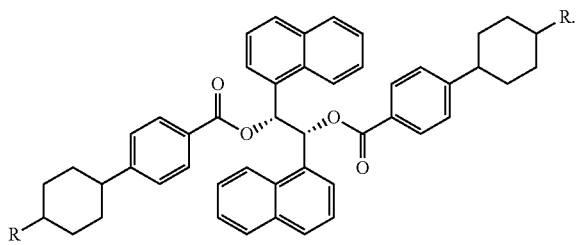

DESCRIPTION OF THE EMBODIMENTS

The present invention is directed to chiral binaphthyl compounds having good solubility and high helical twisting power (HTP). The chiral binaphthyl compounds can be applied in the liquid crystal compositions for the liquid crystal panels. The chiral binaphthyl compounds can function as dopants and be mixed with the liquid crystals in various ratios. By means of the resulting liquid crystal composition containing chiral binaphthyl compounds of the present invention, the liquid crystal panels can afford high voltage holding ratios, thus lessening the image retention and improving the display contrast.

The optical characteristics of the liquid crystal molecules can be modified or changed by adding the dopants. The chiral binaphthyl compounds of the present invention may function as dopants for the liquid crystal compositions.

The "liquid crystal" refers to any commonly used liquid crystal for the liquid crystal panels or liquid crystal monitors, including but not limited to, nematic liquid crystal or cholesteric liquid crystal. The modification or adjustment of the liquid crystal compositions is encompassed within the scope of the present invention.

The present invention provides chiral binaphthyl compounds having the structure of the following formula (I):

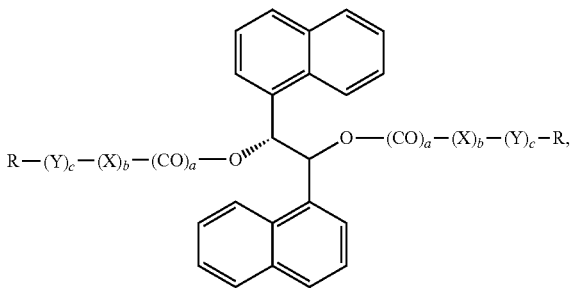

wherein Y is a repeating unit represented as —($A^1$—Z)m—$A^2$—, $A^1$ and $A^2$ can be cyclic structures respectively selected from the following group:

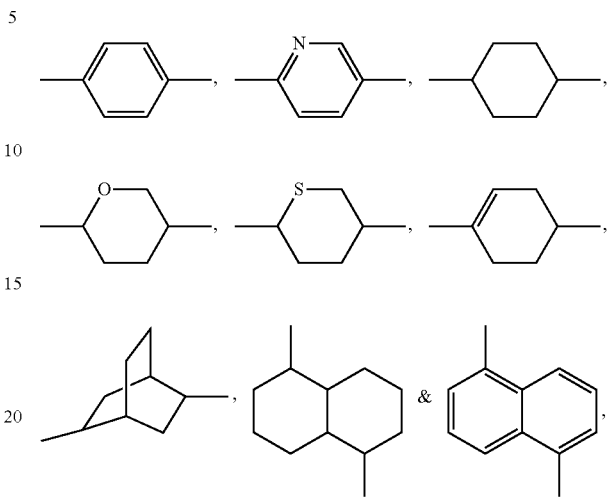

X and Z can be the same or different linking groups selected from the following group consisting of
—O—, —S—, —CO—, —COO—, —OCO—, —O—COO—, —CO—N($R^1$)—, —N($R^1$)—CO—, —OCH$_2$—, —CH$_2$O—, —SCH$_2$—, —CH$_2$S—, —CF$_2$O—, —OCF$_2$—, —CF$_2$S—, —SCF$_2$—, —CH$_2$CH$_2$—, —CF$_2$CH$_2$—, —CH$_2$CF$_2$—, —CF$_2$CF$_2$—, —CH=CH—, —CF=CH—, —CH=CF—, —CF=CF—, —C≡C—, —CH=CH—COO— and a single bond, a, b & c are individually 0, 1 or 2, m is 0, 1, 2 or 3, and R is a straight-chained or branched $C_1$~$C_{30}$ alkyl group, a straight-chained or branched $C_1$~$C_{30}$ alkyl group of which one or more —CH$_2$— being substituted with —O—, —S—, —NH—, —N(CH$_3$)—, —CO—, —CO—O—, —O—CO—, —CH=CH— or —C≡C—, or the above-mentioned alkyl group being selectively substituted with —F, —Cl, —Br, —NCS, —CN, or —OCF$_3$.

The chiral binaphthyl compounds of the present invention can be prepared based on the commonly used preparation methods or synthesis processes in the organic chemistry field. Depending on the various substitutional groups, the solvents, reaction parameters, reaction temperatures or additives can be accordingly adjusted or changed. Such adjustments should not be limited to the embodiments provided herein and is well understood by the artisan.

EXPERIMENT

The synthesis of the chiral binaphthyl compound is shown in the following Reaction Scheme (II):

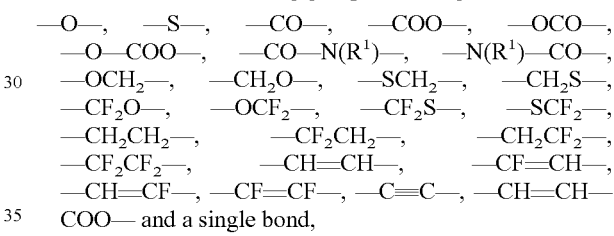

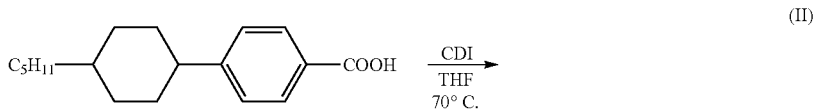

-continued

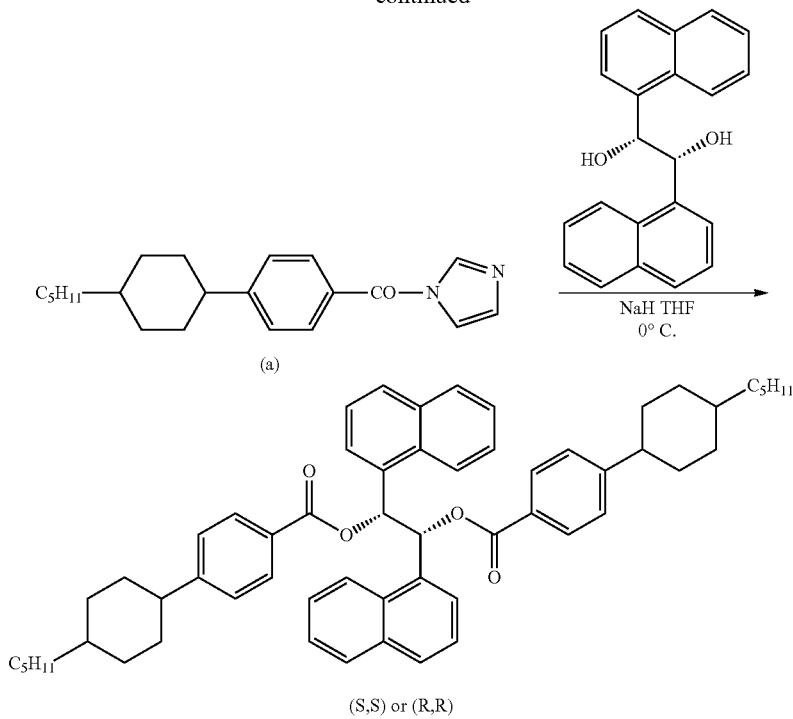

8 mmol of 4-(trans-4-pentylcyclohexyl)benzoic acid and 20 ml of dry THF were placed in the reaction flask. After complete dissolution, the mixture was heated up. Once it reached the reflux temperature, 12 mmol of 1,1'-carbonyldiimidazole (CDI) was added and the mixture was stirred overnight until the clear mixture solution turned into a yellow solution. The reaction solution was cooled to the room temperature and vacuum concentrated to remove THF, so as to obtain a yellow solid. Extracted with dichloromethane and water, the organic layer is retained and treated with dry magnesium sulfate, then vacuum concentrated to obtain an intermediate product (a) 2.96 g (9.2 mmol).

Furthermore, 3.2 mmol of (S,S)-1,2-di(1-napthyl)-1,2-ethanediol and dry THF (20 ml) are placed in the reaction flask. After complete dissolution, the mixture was ice-bathed until reaching 0° C. and sodium hydride (7.6 mmol) was added slowly and stir-reacted for 10 minutes. Later, after adding the obtained intermediate product (a) 2.96 g (9.2 mmol), the reaction temperature of the mixture was increased slowly back to the room temperature and the mixture was stir-reacted for an hour. When the reaction complete, the reaction solution was vacuum concentrated to remove THF and a yellow liquid is obtained. Extracted with dichloromethane and water, the organic layer is retained and treated with dry magnesium sulfate, then vacuum concentrated to obtain the yellow crude product 2.2 g. Recrystallization with isopropyl ether and methanol overnight and vacuum dry up, 2.01 g (2.4 mmol) of a white flake crystal product is obtained. The yield is about 76.3%.

By using the above Reaction Scheme (II), the following compounds (b), which has the formula (I) when a=1, b=0, c=1, m=1 and Z is a single bond, can be synthesized.

Where product 1: R=$C_5H_{11}$, with the yield of 76.3%, Tm 167° C., with $^1$H NMR (400 MHz, CDCl$_3$) verified: σ 8.32 (s, 2H), 7.99 (d, J=8.0 Hz, 4H), 7.71 (d, J=8.0 Hz, 2H), 7.63 (d, J=8.1 Hz, 2H), 7.50 (s, 2H), 7.45 (s, 2H), 7.39 (q, J=13.5, 6.4 Hz, 4H), 7.22 (q, J=16.6, 7.9 Hz, 6H), 2.49 (t, J=12.0 Hz, 2H), 1.86 (d, J=9.3 Hz, 8H), 1.43 (q, J=23.0, 11.6 Hz, 4H), 1.32 (t, J=6.03 Hz, 8H), 1.28 (d, J=9.4 Hz, 8H), 1.25 (s, 2H), 1.07 (q, J=23.1, 12.1 Hz, 4H), 0.90 (t, J=6.7 Hz, 6H).

Where product 2: R=$C_7H_{15}$, with the yield of 74.5%, Tm 153° C., with $^1$H NMR (400 MHz, CDCl$_3$) verified: σ 8.31 (s, 2H), 7.98 (d, J=8.2 Hz, 4H), 7.70 (d, J=8.3 Hz, 2H), 7.63 (d, J=8.2 Hz, 2H), 7.50 (s, 2H), 7.44 (s, 2H), 7.39 (q, J=12.9, 6.1 Hz, 4H), 7.22 (q, J=16.4, 8.0 Hz, 6H), 2.49 (t, J=12.0 Hz, 2H), 1.86 (d, J=9.6 Hz, 8H), 1.38 (q, J=23.1, 12.1 Hz, 4H), 1.28 (s, 22H), 1.24 (s, 4H), 1.04 (q, J=23.0, 10.8 Hz, 4H), 0.89 (t, J=6.1 Hz, 6H).

The above mentioned chiral binaphthyl compounds are added to the active matrix liquid crystal compositions and compared with the common doped liquid crystal compositions as shown in Table 1.

TABLE 1

| Dopant | S-811 | S-1011 | R-1011 | Product 1 | Product 2 |
|---|---|---|---|---|---|
| HTP ($\mu m^{-1}$) | 12 | 37 | 34 | 42 | 41 |
| Dopant adding ratio (wt %) | 20 | 6.5 | 6.5 | 6 | 6 |
| VHR (%) of Doped active matrix liquid crystal composition 1 (JM-2069-051) | 49 | 83 | 81 | 93 | 92 |

TABLE 1-continued

| Dopant | S-811 | S-1011 | R-1011 | Product 1 | Product 2 |
|---|---|---|---|---|---|
| VHR (%) of Doped active matrix liquid crystal composition 2 (JM-2069-054) | 53 | 85 | 82 | 96 | 94 | ps: VHR of the undoped active matrix liquid crystal composition being 100%, reflective wavelength 550 nm. Doped active matrix liquid crystal composition 1 or 2 has different dopants in different ratios, but both compositions 1 & 2 are fluro-containing formulations.

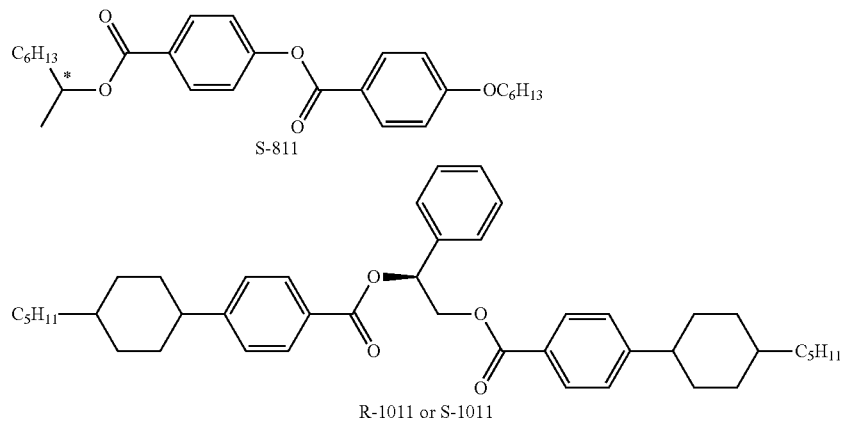

S-811

R-1011 or S-1011

By adding the products 1 & 2 to the active matrix liquid crystal compositions, the doped liquid crystal compositions can afford VHRs $\geqq$90%. Since the products 1 & 2 have HTPs $\geqq$40 $\mu m^{-1}$, the addition amounts of the products 1 & 2 can be lesser compared with the conventional dopants under the same wavelength. Compared with the conventional dopants shown in Table 1, the chiral binaphthyl compounds of this invention can provide better optical effects and suitable for various types of liquid crystal compositions.

According to embodiments of the present invention, the exemplary chiral binaphthyl compounds are listed in Table 2. However, the examples provided herein merely covers a portion of the compounds covered by the formula (I) and the exemplary a, b, c, m, or the substitutional or functional groups shown as X, Y, Z, $A^1$, $A^2$ or R are simply representative and should not be used to limit the scope of the invention.

TABLE 2 a = 0, b = 1, c = 0

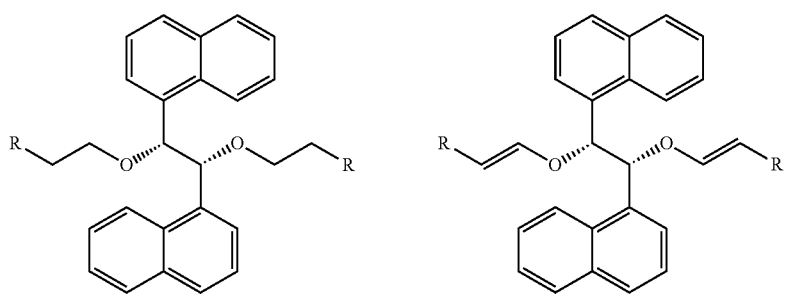

TABLE 2-continued
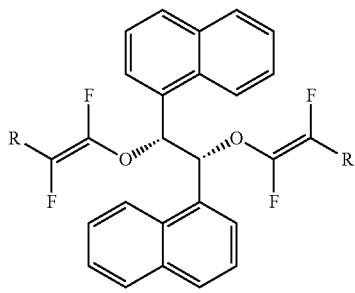 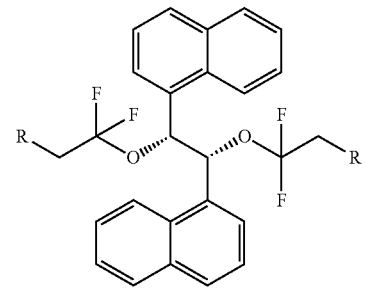
a = 1, b = 0, c = 1
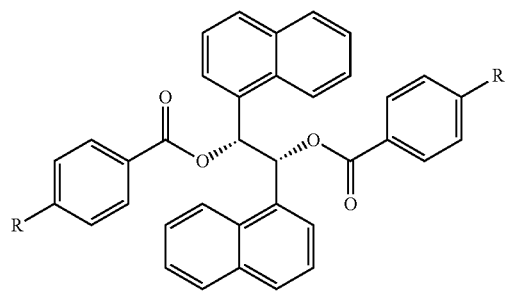
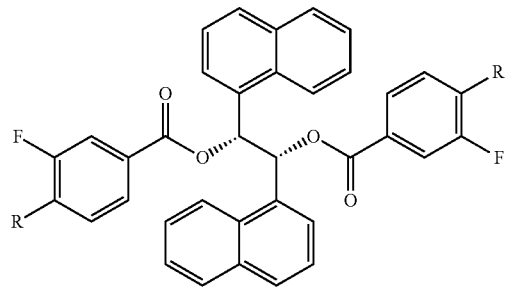
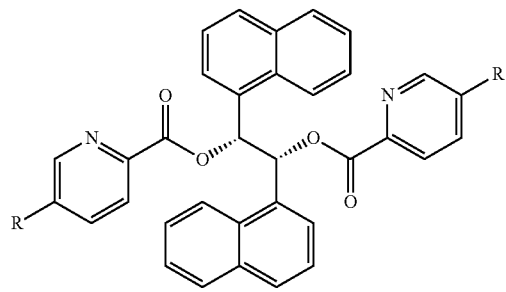
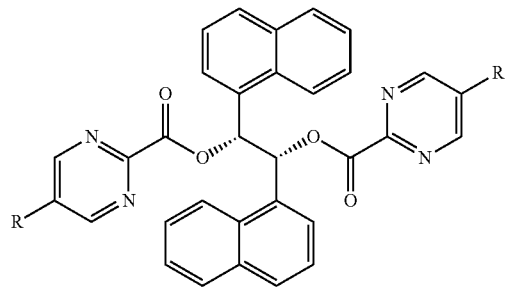

TABLE 2-continued
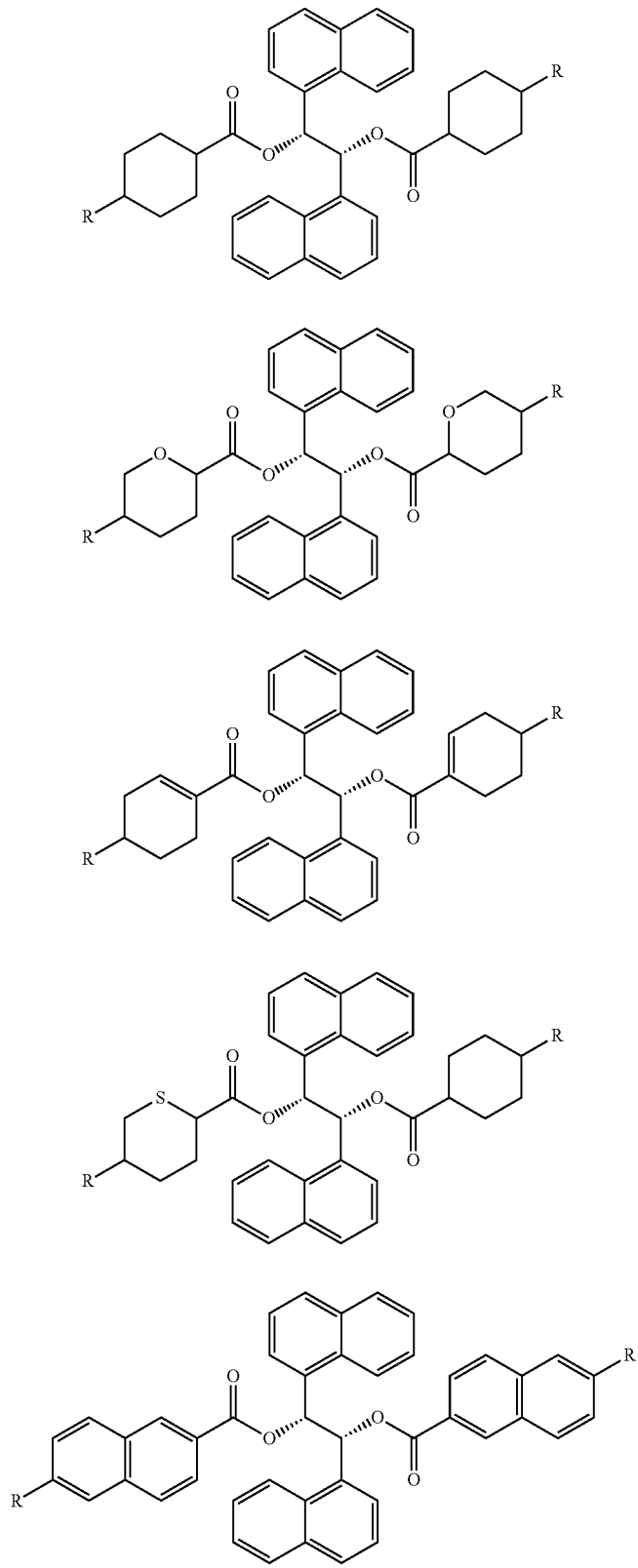

TABLE 2-continued
a = 1, b = 0, c = 2
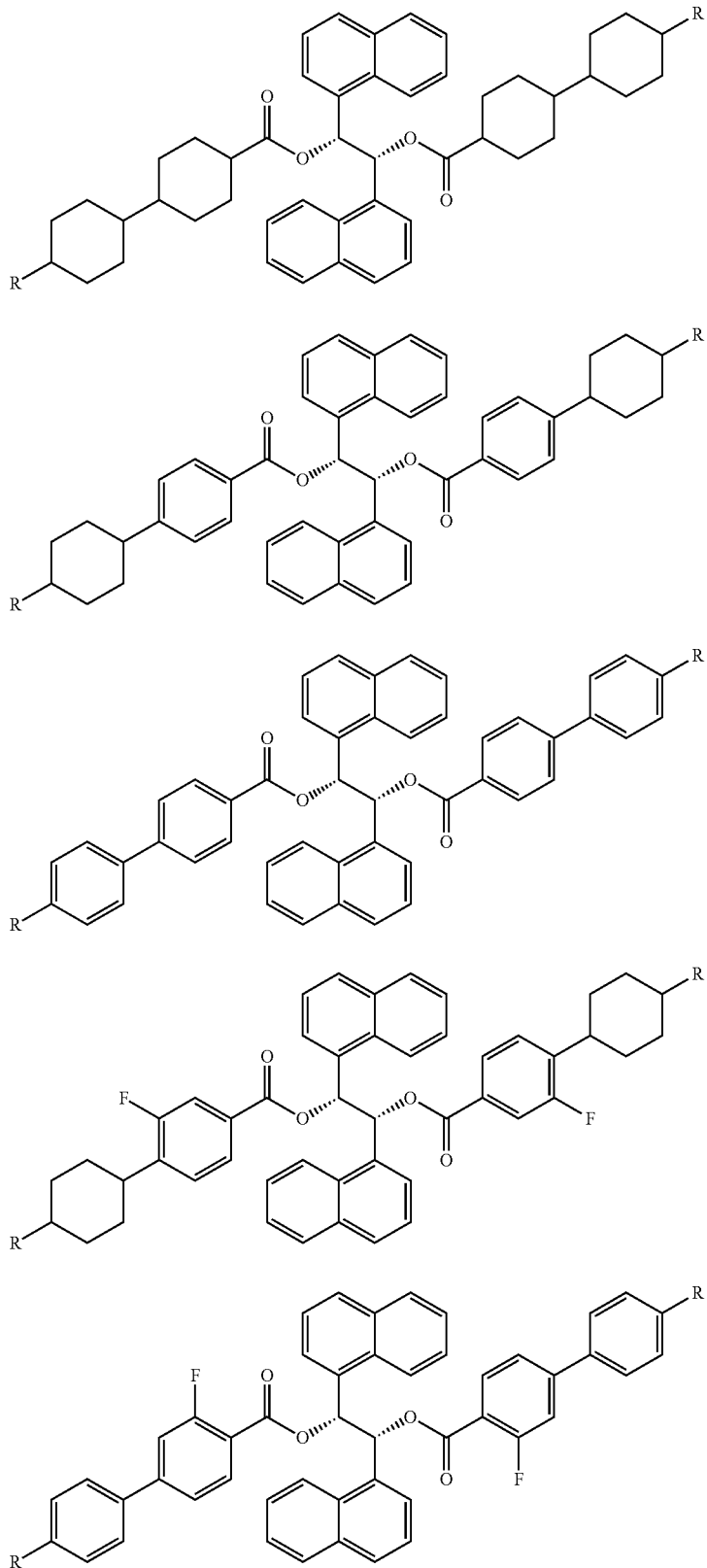

TABLE 2-continued
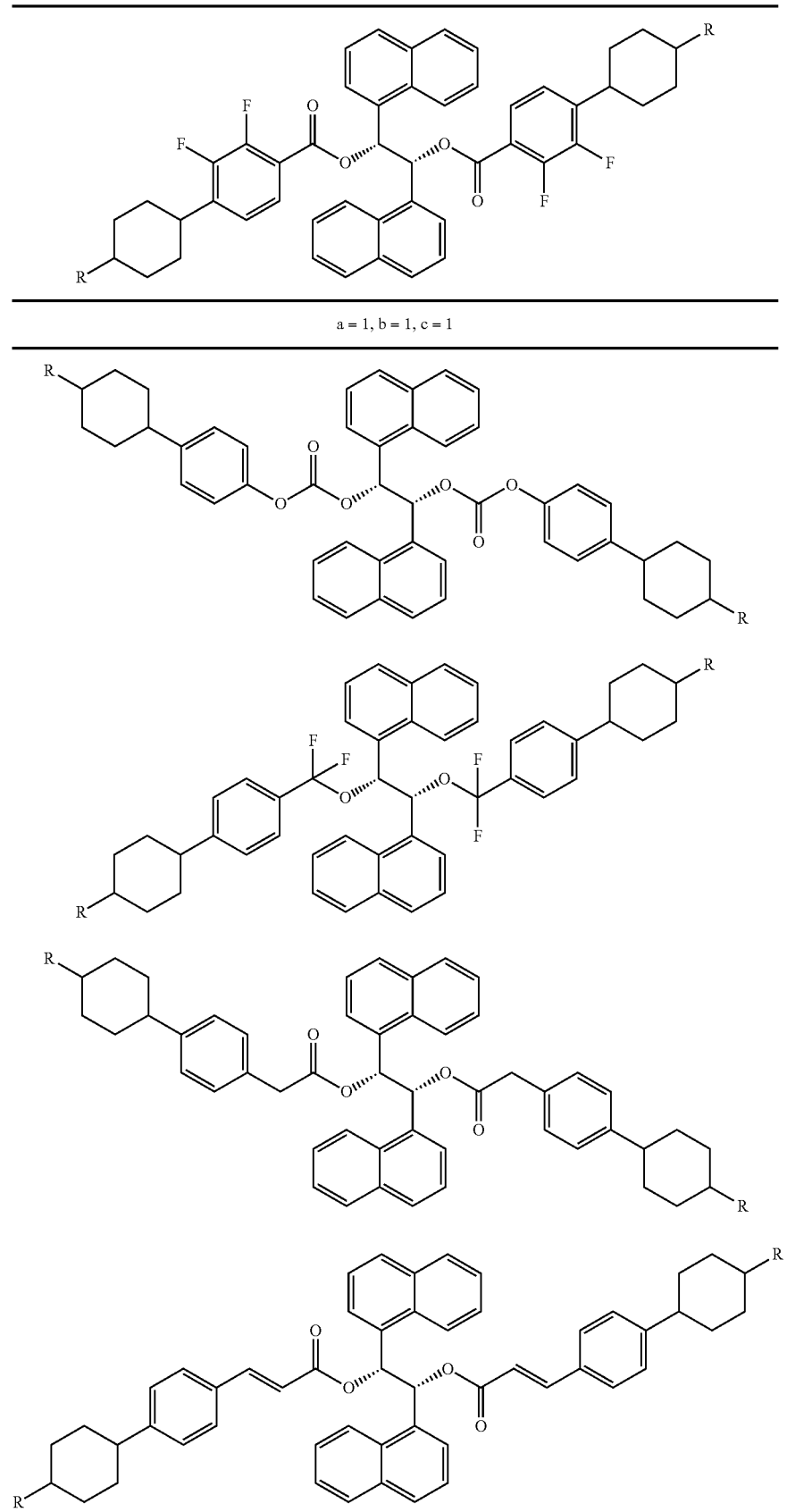
a = 1, b = 1, c = 1

TABLE 2-continued
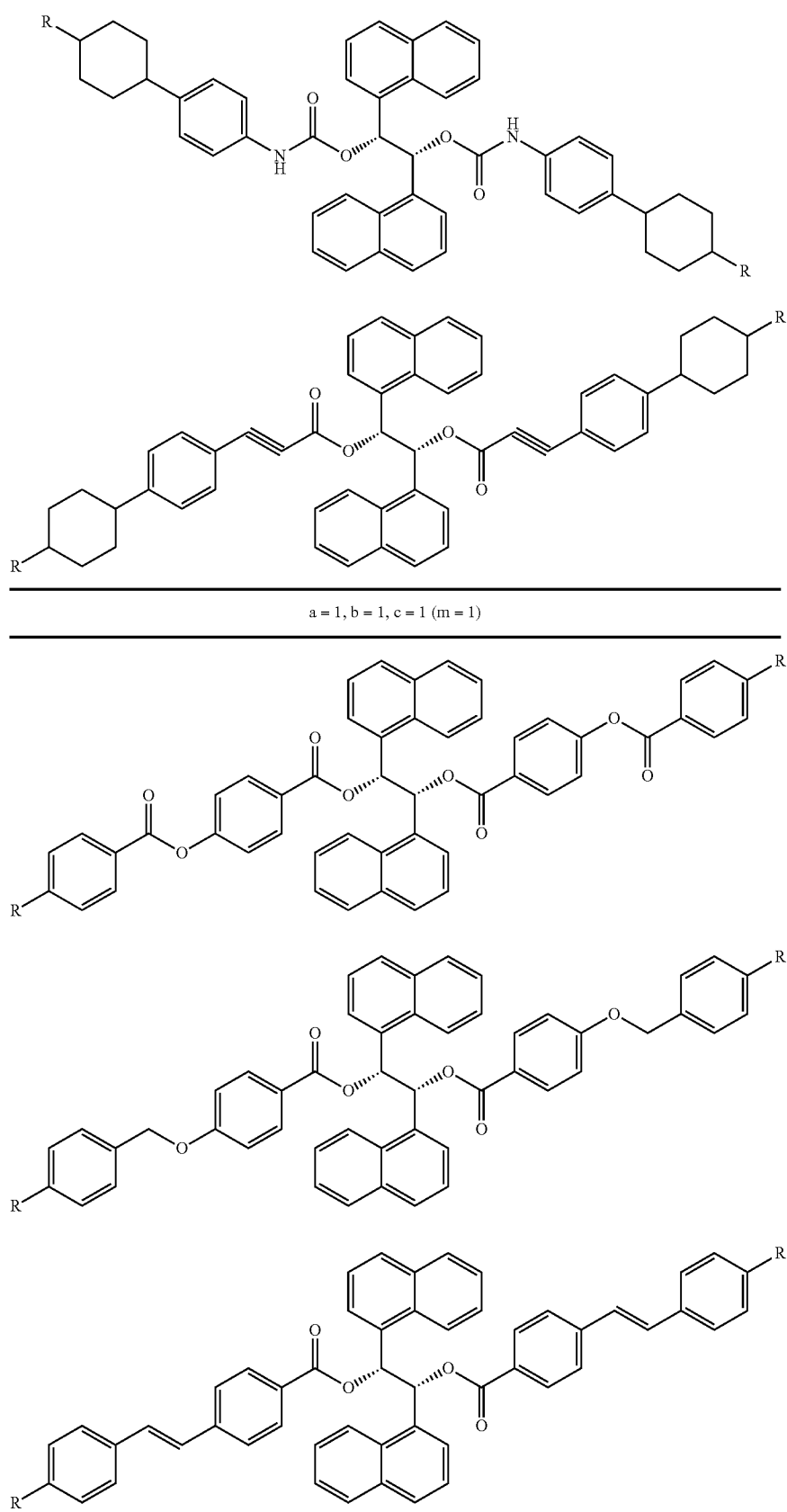
a = 1, b = 1, c = 1 (m = 1)

TABLE 2-continued
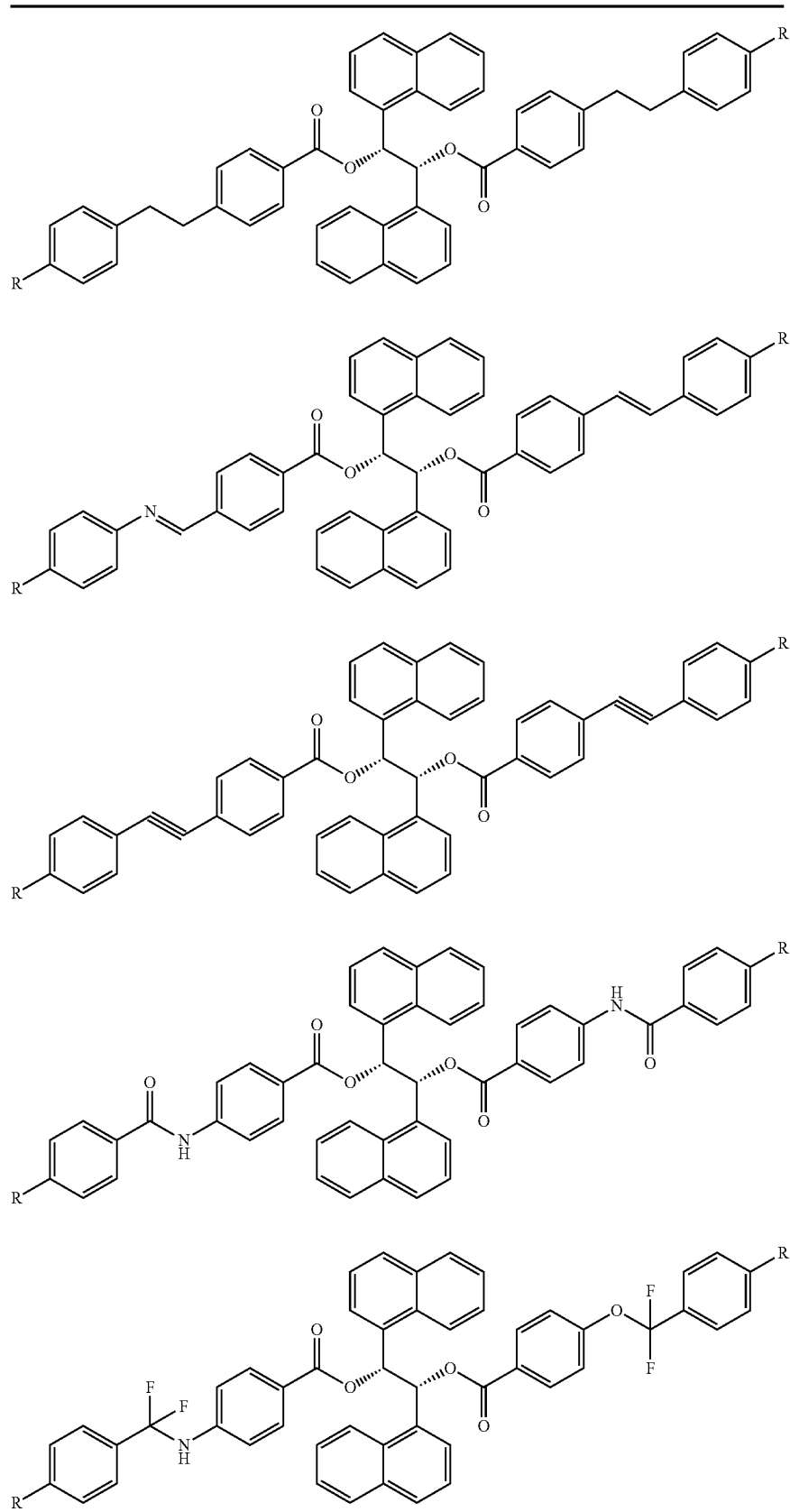

TABLE 2-continued
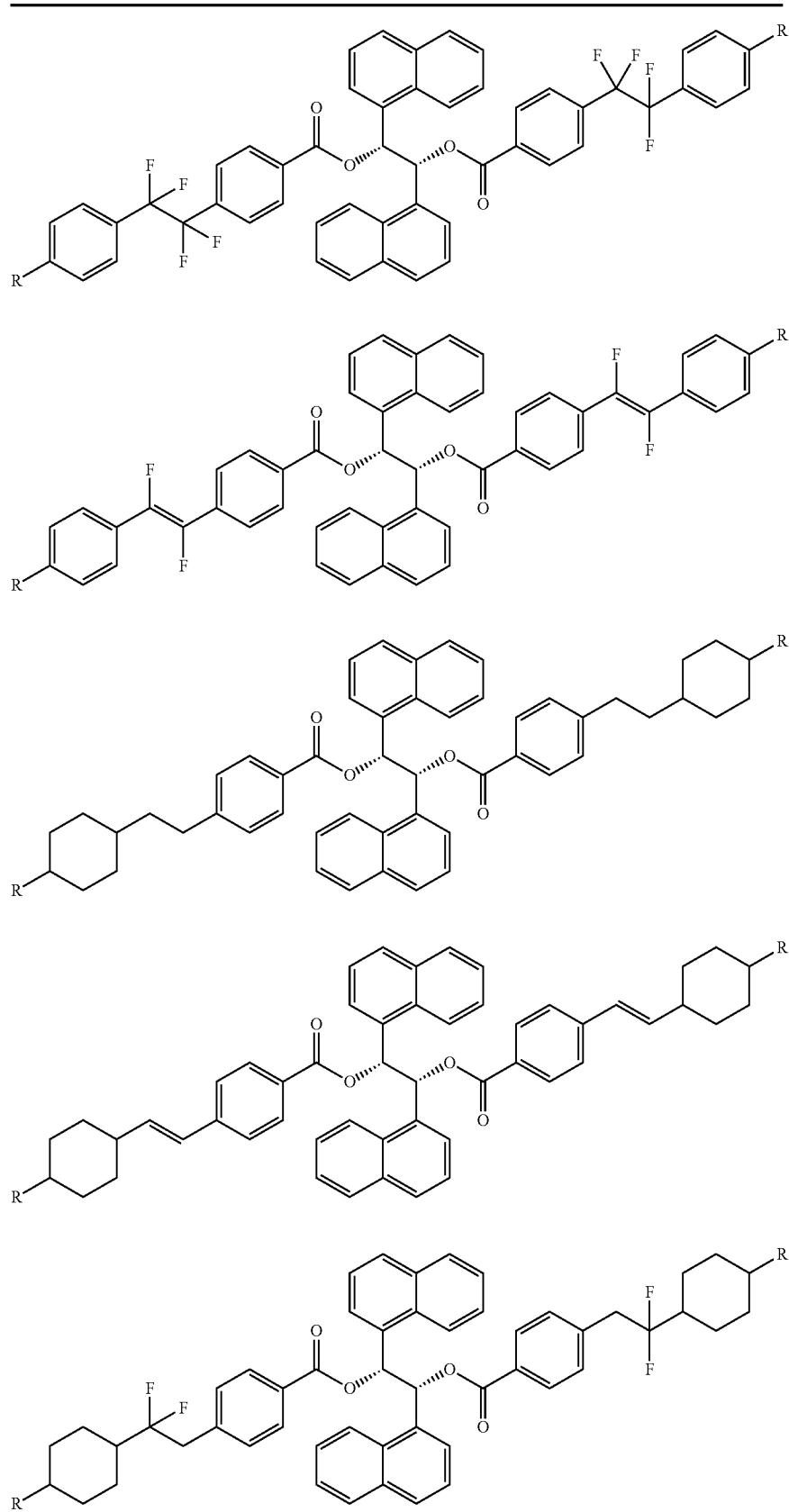

TABLE 2-continued

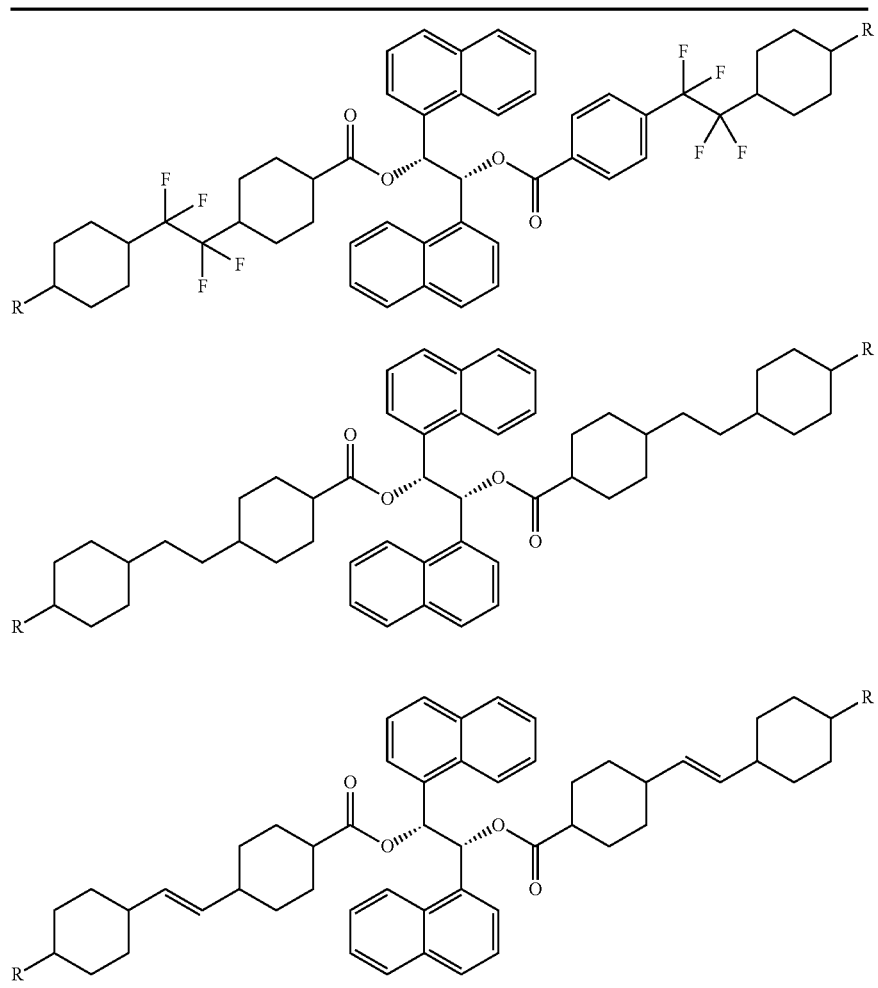

While the invention has been described and illustrated with reference to specific embodiments thereof, these descriptions and illustrations do not limit the invention. It should be understood by those skilled in the art that various changes may be made and equivalents may be substituted without departing from the true spirit and scope of the invention as defined by the appended claims. The illustrations may not be necessarily being drawn to scale. There may be distinctions between the artistic renditions in the present disclosure and the actual apparatus due to manufacturing processes and tolerances. There may be other embodiments of the present invention which are not specifically illustrated. The specification and the drawings are to be regarded as illustrative rather than restrictive. Modifications may be made to adapt a particular situation, material, composition of matter, method, or process to the objective, spirit and scope of the invention. All such modifications are intended to be within the scope of the claims appended hereto. While the methods disclosed herein have been described with reference to particular operations performed in a particular order, it will be understood that these operations may be combined, sub-divided, or re-ordered to form an equivalent method without departing from the teachings of the invention.

What is claimed is:

1. A chiral binaphthyl compound selected from the following group consisting of

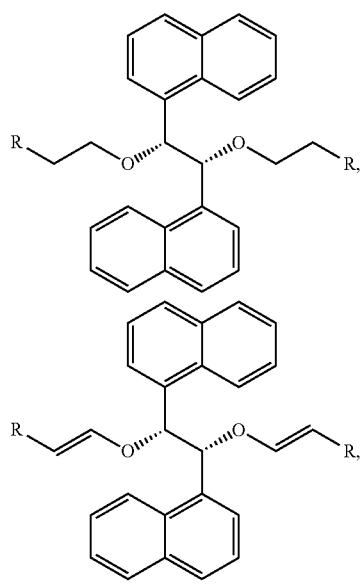

25
-continued
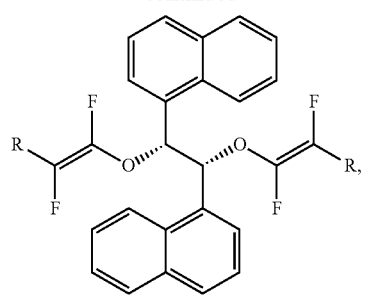
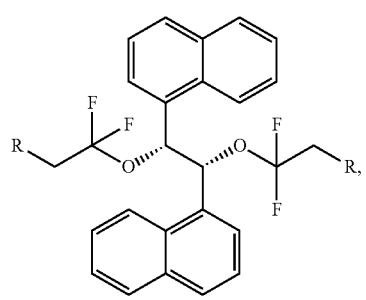
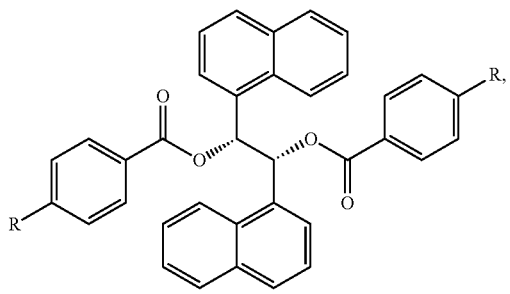
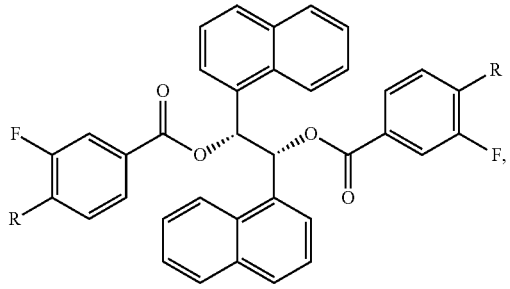
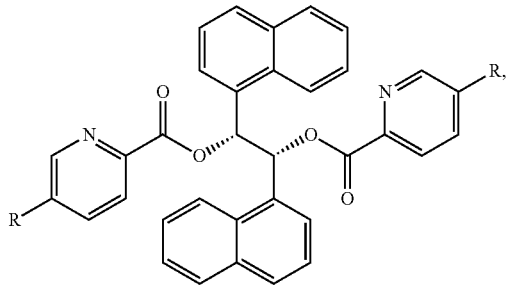
26
-continued
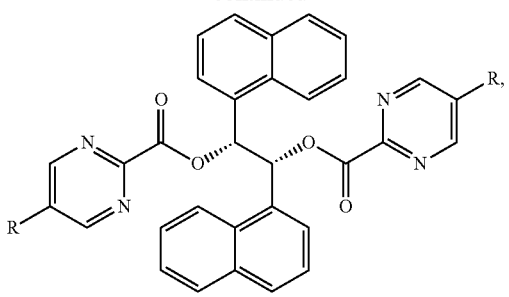
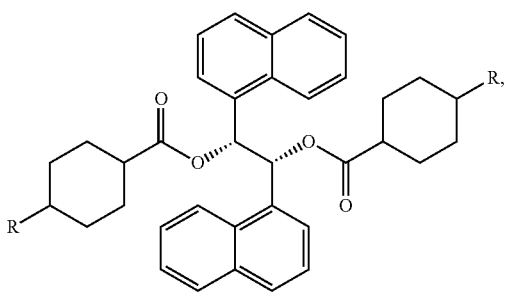
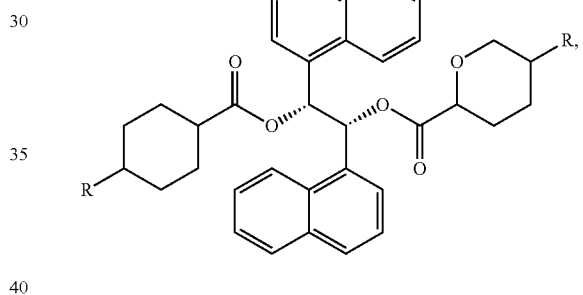
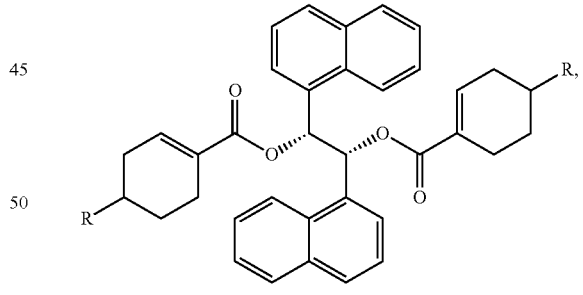
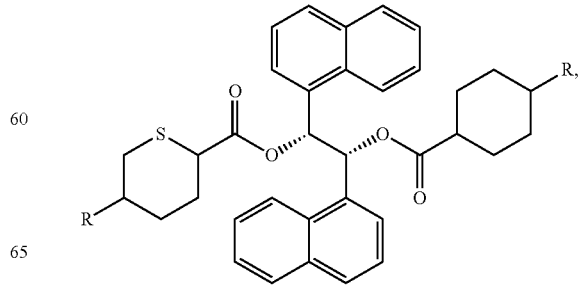

27
-continued

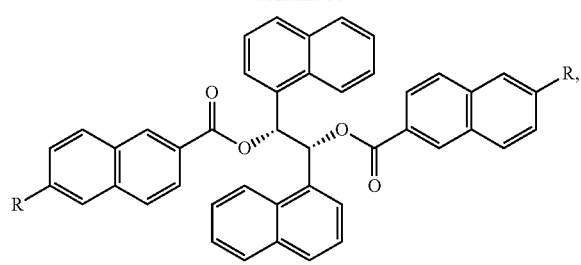

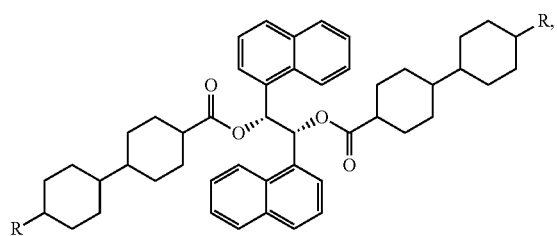

28
-continued

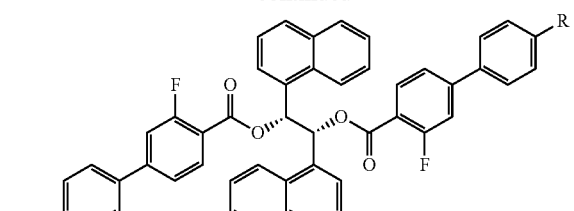

and

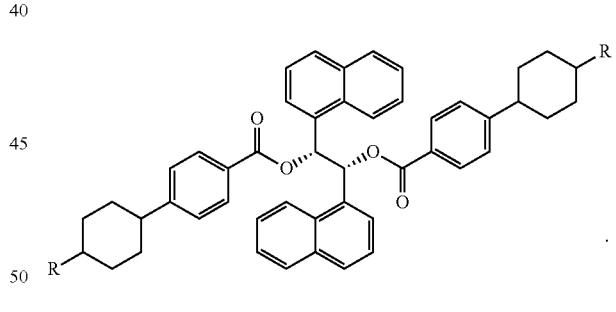

wherein R is a straight-chained or branched $C_1$-$C_{30}$ alkyl group of which one or more $CH_2$ is optionally substituted with —O—, —S—, —NH—, —N($CH_3$)—, —CO—, —CO—O—, —O—CO—, —CH=CH— or —C≡C—, or the above-mentioned alkyl group being selectively substituted with —F, —Cl, —Br, —NCS, —CN, or —OCF$_3$.

2. The compound of claim 1, wherein the compound has the following chemical structure, and R=$C_5H_{11}$

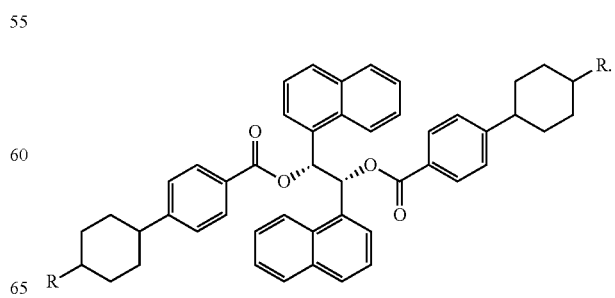

3. The compound of claim 1, wherein the compound has the following chemical structure, and R=$C_7H_{15}$ 4. A chiral binaphthyl compound selected from the following group consisting of
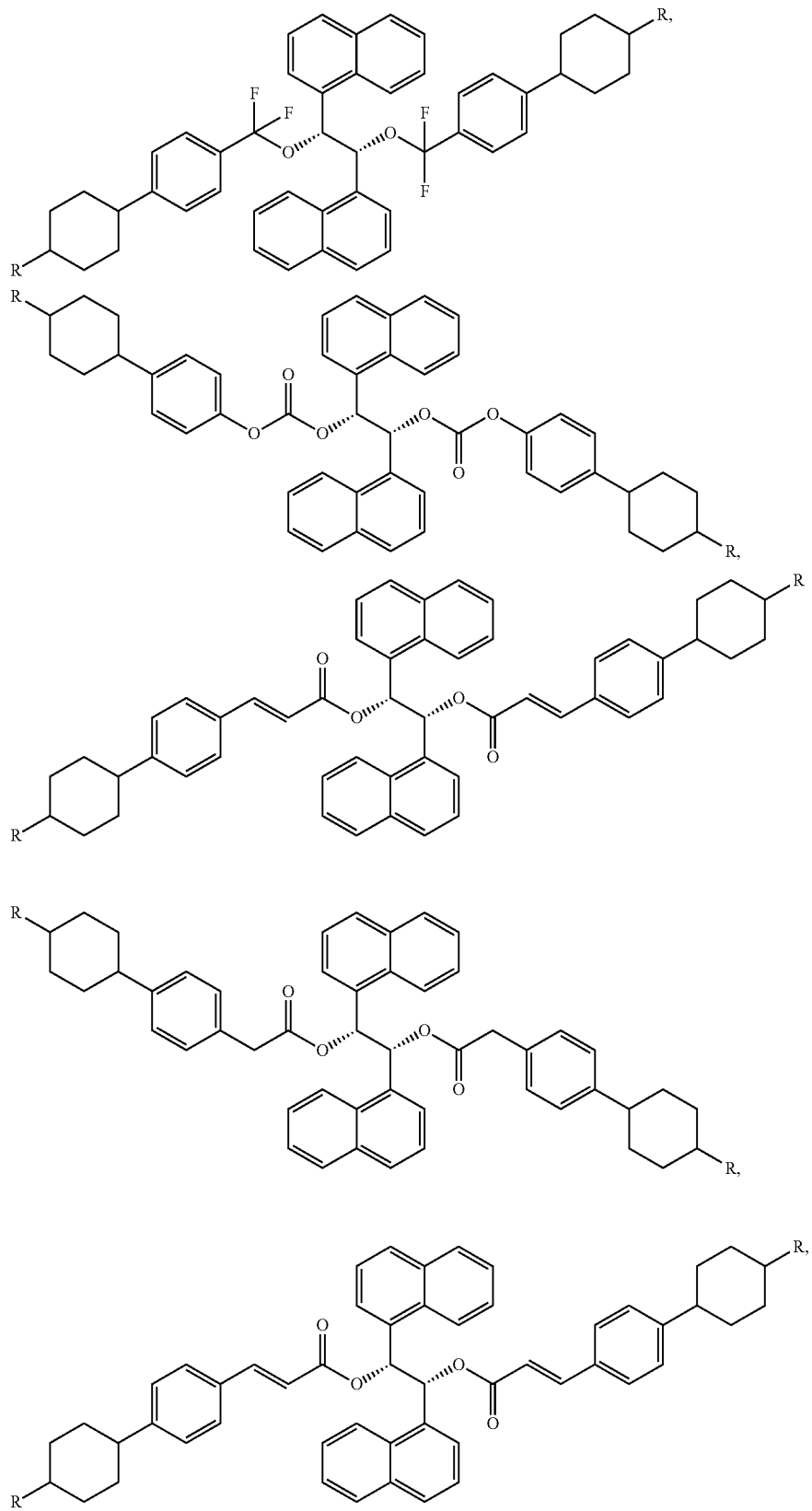

-continued
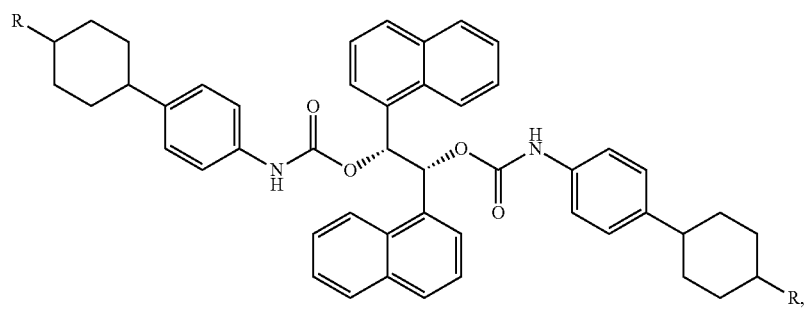
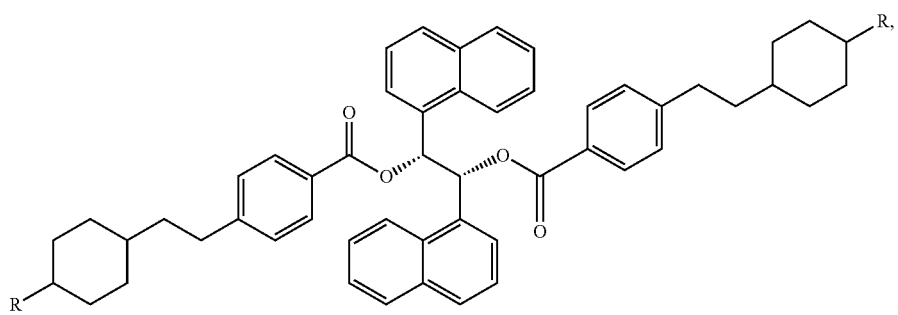
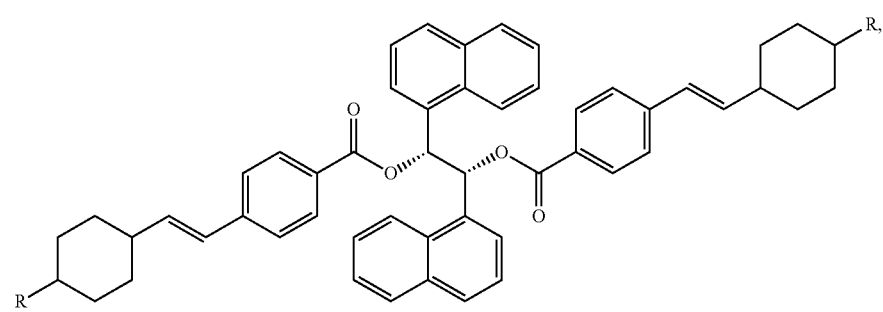
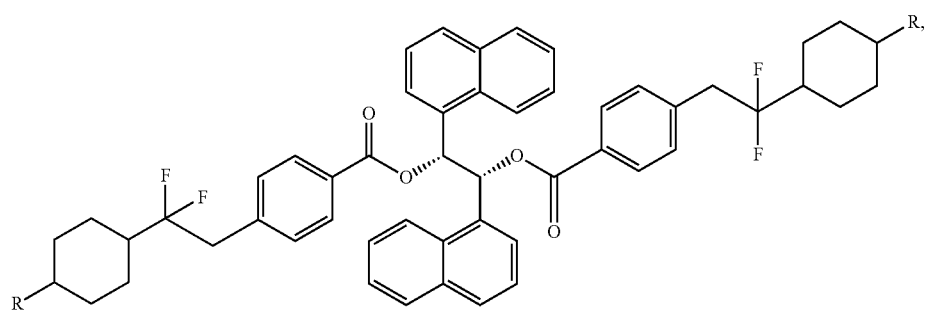
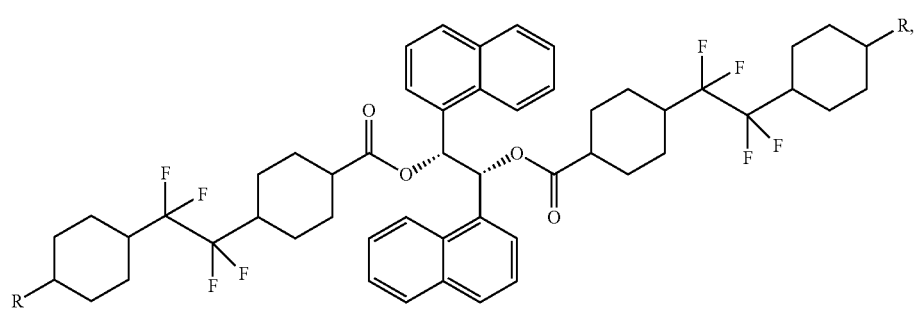

-continued
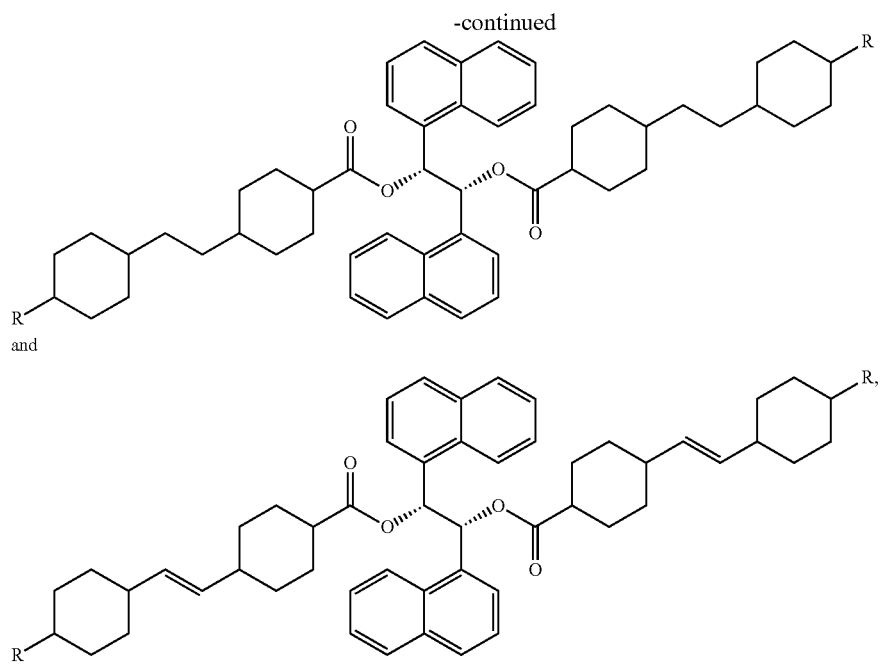
and
wherein R is a straight-chained or branched $C_1$~$C_{30}$ alkyl group of which one or more —$CH_2$— is optionally substituted with —O—, —S—, —NH—, —N($CH_3$)—, —CO—, —CO—O—, —O—CO—, —CH=CH— or —C≡C—, or the above-mentioned alkyl group being selectively substituted with —F, —Cl, —Br, —NCS, —CN, or —$OCF_3$.
* * * * *